United States Patent [19]
Brockway

[11] Patent Number: 5,407,351
[45] Date of Patent: * Apr. 18, 1995

[54] APPARATUS FOR SUPPORTING AND CONTROLLING FLUID DELIVERY TO A DENTAL HANDPIECE

[75] Inventor: Charles E. Brockway, Fairview, N.C.

[73] Assignee: Knight Manufacturing Inc., Asheville, N.C.

[ * ] Notice: The portion of the term of this patent subsequent to Feb. 9, 2010 has been disclaimed.

[21] Appl. No.: 136,452

[22] Filed: Oct. 14, 1993

[51] Int. Cl.⁶ ................................. A61C 1/02
[52] U.S. Cl. .......................... 433/28; 433/77
[58] Field of Search ............ 433/28, 77, 78, 80, 433/84

[56] References Cited

U.S. PATENT DOCUMENTS

| | | | |
|---|---|---|---|
| 2,287,058 | 6/1942 | Pieper | 433/77 |
| 3,986,262 | 10/1976 | Casillas. | |
| 4,117,861 | 10/1978 | Betush | 137/595 |
| 4,345,616 | 8/1982 | Terry | 433/78 |
| 4,375,963 | 3/1983 | Betush | 433/28 |
| 5,145,366 | 9/1992 | Janhunen | 433/77 |
| 5,158,453 | 10/1992 | Brockway | 433/28 |

Primary Examiner—Cary E. O'Connor
Attorney, Agent, or Firm—Shefte, Pinckney & Sawyer

[57] ABSTRACT

An apparatus for supporting and controlling fluid delivery to a dental handpiece includes a frame with a holder for receiving the handpiece, a support arm connected with the handpiece and pivoted to the frame, an actuating linkage operated by the support arm, and fluid delivery tubing which extends to the handpiece being affixed at spaced locations to the frame and to the actuating linkage for folding of the tubing upon itself to close the tubing against fluid flow when the handpiece is mounted in its holder and for unfolding the tubing for open fluid flow when the handpiece is removed from the holder.

8 Claims, 2 Drawing Sheets

APPARATUS FOR SUPPORTING AND CONTROLLING FLUID DELIVERY TO A DENTAL HANDPIECE

BACKGROUND OF THE INVENTION

The present invention relates generally to dental office equipment of the type commonly used in dentists' offices for routine patient procedures. More particularly, the present invention relates to a novel apparatus for supporting and controlling delivery of fluids, such as air and water, to a dental handpiece, such as a dentist's drill.

Currently, conventional equipment used by practicing dentists typically comprises a variety of hand-held power-operated tools for performing differing dental procedures, one of the most common and familiar of which, by way of example, is a drill used for removing decayed portions of teeth preparatory to filling with a protective material. Typically, such drills and like dental handpieces are driven by compressed air and it is also commonplace for a cooling fluid, usually air, water or a mixture thereof, to be delivered to the handpiece for emission into the drilling or other work area for cooling purposes.

To facilitate convenient usage of such handpieces by dentists, a conduit system is provided in the dentist's office to provide a ready source of compressed air and pressurized water and is equipped with an associated valving system, normally actuated and deactuated through a foot-operated device, to enable the dentist to selectively control fluid delivery to the dental handpieces being utilized.

In the past, such valving systems have been relatively complicated and, in turn, costly, not only to manufacture but also to service when in need of repair. Accordingly, a need has existed for a simplified and less costly form of valve system for controlling delivery of operating fluids to dental handpieces.

U.S. Pat. No. 4,375,963, represents a relatively recent development addressing this problem and need. Basically, this patent discloses a control unit for dental handpieces wherein a handpiece holder is carried on a pivoting support arm mounted to a suitable frame member. A resiliently flexible tube is attached to the handpiece and extends therefrom through the frame member in a configuration tending to urge the support arm into an upwardly pivoted position when the handpiece is removed from the holder. An actuator is mounted in a stationary position on the frame member adjacent the holder for engagement by the handpiece when inserted into the holder to cause the support arm to pivot into a downward position. In such position, opposing pinch members mounted on the frame member and the support arm are moved into sufficiently close proximity to one another to physically clamp the flexible tube between the pinch members and thereby close the tube to prevent further fluid flow to the handpiece. Upon subsequent removal of the handpiece from the holder, the natural resiliency of the tube urges the support arm into its upward disposition, thereby separating the pinch members to allow fluid flow through the tube.

SUMMARY OF THE INVENTION

It is an object of the present invention to provide an equally simplified apparatus for supporting and controlling delivery of an operating fluid for a dental handpiece which avoids the necessity of physically pinching fluid delivery tubing to accomplish opening and closing thereof, but rather operates to close and open the tubing by folding and unfolding, i.e., kinking and unkinking, the tubing without physically contacting the tubing at the fold location.

Briefly summarized, the apparatus of the present invention basically comprises a frame member having a holder mounted thereon for receiving the dental handpiece and a support arm for connection of the dental handpiece therewith, the support arm being movably mounted to the frame member to move between a first position when the dental handpiece is received by the holder and a second position when the dental handpiece is removed from the holder. An actuator is associated with the support arm for movement therewith between a deactuating position when the support arm is in its first position and an actuating position when the support arm is in its second position. Tubing is provided for delivering the operating fluid for the dental handpiece, the tubing being affixed at spaced locations therealong respectively to the frame member and to the actuator to define a fixed length of the tubing therebetween. When the actuator is in its deactuating position, the fixed length of the tubing is folded upon itself to prevent fluid flow through the tubing. When the actuator is in its actuating position, the tubing is sufficiently relaxed to permit fluid flow therethrough.

In the preferred embodiment, the actuator is arranged to move the spaced locations of affixation of the tubing toward and away from one another upon movement of the support arm between its first and second positions. In particular, the frame member rotatably supports a first tube connection pin and the actuator rotatably supports a second tube connection pin, with the tubing being affixed to the tube connection pins in diametrical relation thereto at the spaced locations along the tubing for unitary rotational movement of the tube connection pins and the tubing upon movement of the support arm.

Preferably, the support arm is pivotably mounted to the frame member and the actuator comprises an actuating linkage pivotably connected to the frame member. More specifically, in the preferred embodiment, an actuating pin is connected with the support arm for arcuate movement into and out of deflecting engagement with the actuating linkage upon pivoting of the support arm between its first and second positions. The preferred actuating linkage comprises a first link pivoted coaxially with the support arm and a second link pivoted to the frame member at a spacing from the support arm, with the first and second links being pivoted to one another. A biasing device such as a spring is provided for urging the actuating pin into engagement with the actuating linkage to normally urge the actuator into its deactuating position.

DETAILED DESCRIPTION OF THE PREFERRED EMBODIMENT

Figure 1:
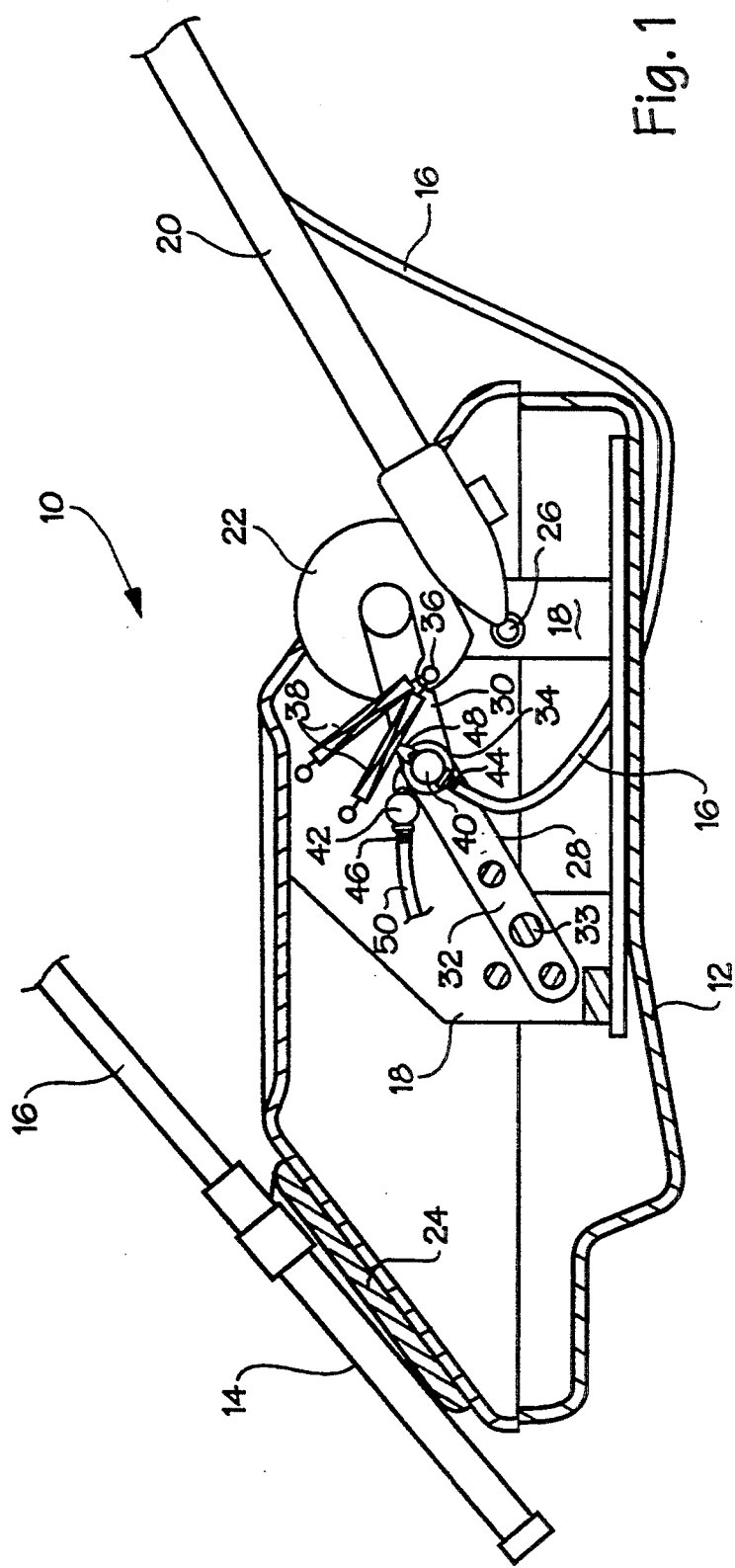
FIG. 1 is a side elevational view, partially in vertical cross-section, of a dental handpiece supporting and controlling apparatus according to a preferred embodiment of the present invention, showing the support arm in its first position with the dental handpiece received in its holder, the actuator in its deactuating position, and the tubing folded upon itself to prevent fluid flow therethrough.

Referring now to the accompanying drawings, a dental handpiece supporting and controlling apparatus unit in accordance with the preferred embodiment of the present invention is shown generally at 10. As those persons skilled in the art will recognize and understand, a plurality of the apparatus units 10 will typically be contained within the same frame or housing 12 in side-by-side relation, with each apparatus unit 10 being connected to an individual respective dental handpiece 14, e.g., a dental drill, to control delivery of operating fluids, e.g., pressurized air and water, to the respective handpiece 14 through appropriate tubing 16. The frame 12 thereby serves as an instrument head and is typically mounted on an articulated support linkage (not shown) in association with a conventional dental chair (also not shown).

The apparatus 10 of the present invention is particularly adapted for use with conventional dental handpieces of the type designed to be powered by pressurized air and also supplied with a pressurized cooling fluid such as water, air or both. However, those persons skilled in the art will readily recognize that the apparatus of the present invention is equally applicable for supporting and controlling any other form of dental handpiece wherein at least one operating fluid is to be selectively supplied to the handpiece during use.

The dental handpiece supporting and controlling apparatus 10 includes a subframe 18 rigidly affixed within the main frame or housing 12. An elongate essentially rigid support arm 20 is fixed to a hub 22 rotationally mounted to the subframe 18 within the main frame 12 for pivotal movement of the support arm 20. The tubing 16 extends along the entire length of the support arm 20 and therefrom to the dental handpiece 14. The forward exterior side of the main frame 12 carries a slotted holder 24 in which the handpiece 14 may be rested when not in use. As will be understood, through the connection of the handpiece 14 to the support arm 20 by the tubing 16, pivotal movement of the support arm 20 is controlled by use of the handpiece 14. Specifically, when the handpiece 14 is rested within its holder 24, the support arm 20 is pivoted rearwardly into the position shown in FIG. 1. When the handpiece 14 is removed from the holder 24 and extended by the dentist or other operator, e.g., for attending to a patient, the support arm 20 is pivoted forwardly into the forwardly inclined disposition shown in FIG. 2. A stop pin 26 is provided on the subframe 18 for limiting the degree of rearward pivoting of the support arm 20 past the position of FIG. 1.

An actuating linkage, generally indicated at 28, is connected between the hub 22 and the subframe 18. Specifically, the actuating linkage 28 includes a first link 30 pivoted at one end coaxially with the hub 22 and a second link 32 pivoted adjacent one end to the subframe 18 at 33, with the other ends of the links 30,32 pivotably connected to one another at 34. An actuating pin 36 is affixed eccentrically to the hub 22 to engage and deflect upwardly the first link 30 when the support arm 20 is pivoted into its rearward position of FIG. 1. A pair of coil springs 38 extend between the subframe 18 and the actuating pin 36 to urge the actuating pin into such disposition.

The pivot 34 between the first and second links 30,32 carries a pin 40 for rotational movement upon pivotal movement of the links 30,32, in parallel relation to the pivot axis of the support arm hub 22. A corresponding pin 42 is similarly mounted rotatably to the subframe 18 at a fixed disposition adjacent and in parallel relation to the pin 40. Each of the pins 40,42 is formed with diametrical bores, each bore receiving a respective tubular fitting 44,46 secured therein to project outwardly from each opposite side of the respective pin 40,42. The fittings 44,46 are communicated with one another by a segment of a relatively flexible tube 48. The opposite end of the fitting 46 is connected to a supply tube 50 which extends from the apparatus 10 through its articulated support linkage to a suitable source of fluid supply (not shown). The opposite end of the fitting 44 is connected to the tubing 16 extending to the handpiece 14.

As will be understood, although the drawings only show a single continuous line of tubing to the handpiece 14, the pins 40,42 may support several corresponding pairs of fittings to accommodate the supply of differing respective pressurized fluids to the associated handpiece 14, e.g., to be usable with conventional dental handpieces powered by pressurized air and also supplied with a pressurized cooling fluid (water, air or both) such as a conventional dental drill wherein the exposed drill bit is operatively connected interiorly with a turbine configured to be rotatably driven by a supply of compressed air with separate supplies of coolant water and air also being delivered for emission from the drill at the drilling location for cooling purposes.

Figure 2:
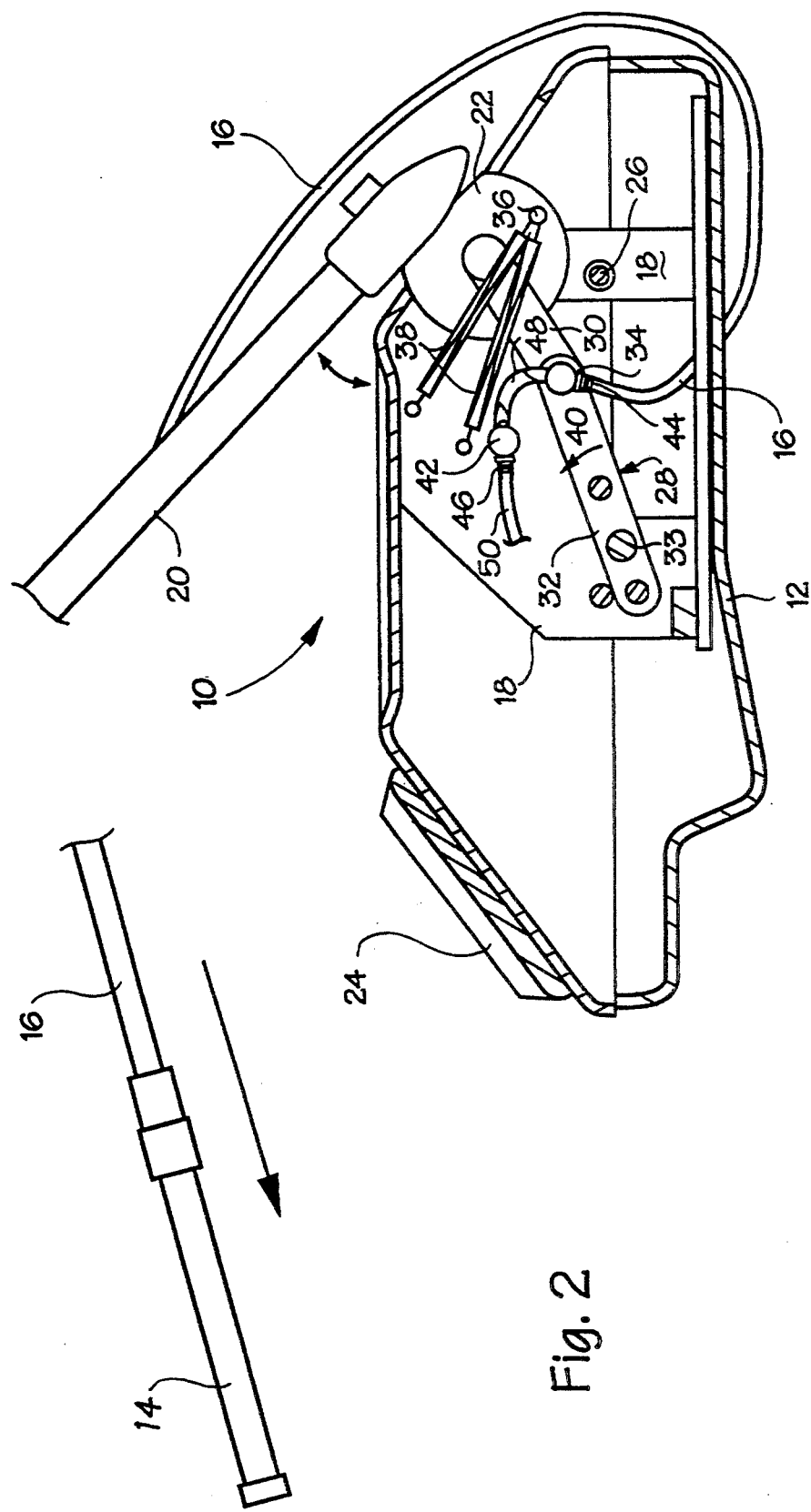
FIG. 2 is another side elevational view similar to FIG. 1, showing the support arm in its second position with the dental handpiece removed from its holder, the actuator in its actuating position, and the tubing relaxed to permit fluid flow.

Normal operation of the handpiece supporting and controlling apparatus 10 of the present invention may thus be understood. When the handpiece 14 is rested in its holder 24 on the frame 12, the support arm 20, as aforementioned, is pivoted rearwardly into the position of FIG. 1. This pivoting action of the support arm 20, in turn, causes the actuating pin 36 to deflect the actuating linkage 28 upwardly by engagement with the first link 30, with the biasing force of the coil springs 38 assisting in this movement. In this disposition of the linkage 28, the tube connection pin 40 supported by the linkage 28 is held in sufficiently close proximity to the tube connection pin 42 on the subframe 18 to cause the tube segment 48 to become folded upon itself into a crimped or kinked configuration sufficient to block fluid flow through the tube segment 48, as shown in FIG. 1. Thus, with the handpiece 14 supported within the holder 24, fluid flow through the tube system of the apparatus 10 is prevented. Upon removal of the handpiece 14 from the holder 24, e.g., to extend the handpiece 14 to a patient, the extending movement of the handpiece 14 acts through the tubing 16 to pivot the support arm 20 forwardly into the inclined disposition of FIG. 2. The corresponding rotational movement of the hub 22 moves the actuating pin 36 away from and out of engagement with the link 30 against the biasing force of the coil springs 38. Without the actuating pin 36 bearing upwardly against the link 30, the linkage 28 is not constrained into the disposition of FIG. 1 and, accordingly, the natural resilient tendency of the flexible tube segment 48 to relax itself acts through the fittings 44,46 to move the actuating pin at the pivot 34 in the actuating linkage 28 away from the tube connection pin 42 sufficiently to permit fluid flow through the tube segment 48.

Those persons skilled in the art will readily recognize that the dental handpiece supporting and controlling apparatus 10 of the present invention is of a simplified construction which is relatively inexpensive to produce and furthermore should operate reliably over a relatively extended useful life.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. Apparatus for supporting and controlling delivery of operating fluid for a dental handpiece, said apparatus comprising a frame member having a holder mounted thereon for receiving the dental handpiece, a support arm for connection of the dental handpiece therewith, said support arm being movably mounted to said frame member to move between a first position when the dental handpiece is received by said holder and a second position when the dental handpiece is removed from said holder, actuator means associated with said support arm for movement therewith between a deactuating position when said support arm is in its said first position and an actuating position when said support arm is in its said second position, and tube means for delivering an operating fluid for the dental handpiece, said tube means being affixed at spaced locations therealong respectively to said frame member and to said actuator means to define a fixed length of said tube means therebetween, said fixed length of said tube means being folded upon itself to prevent fluid flow therethrough when said actuator means is in its deactuating position and being sufficiently relaxed to permit fluid flow therethrough when said actuator means is in its actuating position.

2. Apparatus for supporting and controlling fluid delivery to a dental handpiece according to claim 1, wherein said actuator means is arranged to move said spaced locations of affixation of said tube means toward and away from one another upon movement of said support arm between said first and second positions.

3. Apparatus for supporting and controlling fluid delivery to a dental handpiece according to claim 2, wherein said frame member rotatably supports a first tube connection pin and said actuator means rotatably supports a second tube connection pin, said tube means being affixed to said tube connection pins in diametrical relation thereto at said spaced locations along said tube means for unitary rotational movement of said tube connection pins and said tube means upon movement of said support arm.

4. Apparatus for supporting and controlling fluid delivery to a dental handpiece according to claim 1, wherein said support arm is pivotably mounted to said frame member and said actuator means comprises an actuating linkage pivotably connected to said frame member.

5. Apparatus for supporting and controlling fluid delivery to a dental handpiece according to claim 4, wherein said actuator means comprises an actuating pin connected with said support arm for arcuate movement into and out of deflecting engagement with said actuating linkage upon pivoting of said support arm between its said first and second positions.

6. Apparatus for supporting and controlling fluid delivery to a dental handpiece according to claim 5 and biasing means for urging said actuating pin into engagement with said actuating linkage to move said actuator means into its said deactuating position.

7. Apparatus for supporting and controlling fluid delivery to a dental handpiece according to claim 5, wherein said actuating linkage comprises a first link pivoted coaxially with said support arm and a second link pivoted to said frame member at a spacing from said support arm, said first and second links being pivoted to one another.

8. Apparatus for supporting and controlling fluid delivery to a dental handpiece according to claim 7, wherein said tube means is affixed at one of said spaced locations to the pivot between said first and second links.

* * * * *